(12) United States Patent
Becker et al.

(10) Patent No.: US 8,121,859 B2
(45) Date of Patent: Feb. 21, 2012

(54) CONTROLLING AND OPTIMIZING PATIENT PATHWAYS WITHIN AND ACROSS HEALTH CARE FACILITIES

(75) Inventors: Michael Becker, Nürnberg (DE); Sultan Haider, Erlangen (DE); Peter Huber, Windsbach (DE)

(73) Assignee: Siemens Aktiengesellschaft, Munich (DE)

( * ) Notice: Subject to any disclaimer, the term of this patent is extended or adjusted under 35 U.S.C. 154(b) by 484 days.

(21) Appl. No.: 12/060,428

(22) Filed: Apr. 1, 2008

(65) Prior Publication Data

US 2009/0248439 A1  Oct. 1, 2009

(51) Int. Cl.
*G06Q 50/00* (2006.01)
(52) U.S. Cl. ......................................................... 705/2
(58) Field of Classification Search .................. 396/310; 455/39; 600/300; 705/2, 3, 8; 342/357.07
See application file for complete search history.

(56) References Cited

U.S. PATENT DOCUMENTS

| | | | |
|---|---|---|---|
| 6,700,533 B1* | 3/2004 | Werb et al. ............... | 342/357.48 |
| 2002/0034384 A1* | 3/2002 | Mikhail ........................ | 396/310 |
| 2002/0165733 A1* | 11/2002 | Pulkkinen et al. ................. | 705/2 |
| 2004/0172305 A1* | 9/2004 | Soerensen et al. ................. | 705/3 |
| 2004/0193449 A1* | 9/2004 | Wildman et al. ................. | 705/2 |
| 2005/0131740 A1* | 6/2005 | Massenzio et al. ................. | 705/2 |
| 2005/0215867 A1* | 9/2005 | Grigsby et al. ............... | 600/300 |
| 2006/0047538 A1* | 3/2006 | Condurso et al. ................. | 705/3 |
| 2006/0053035 A1* | 3/2006 | Eisenberg ........................ | 705/2 |
| 2006/0173713 A1* | 8/2006 | Petro et al. ......................... | 705/2 |
| 2006/0173725 A1* | 8/2006 | Abraham et al. ................. | 705/8 |
| 2006/0240771 A1* | 10/2006 | Graves et al. ................... | 455/39 |
| 2008/0255880 A1* | 10/2008 | Beller et al. ...................... | 705/3 |

* cited by examiner

*Primary Examiner* — Gerald J. O'Connor
*Assistant Examiner* — John Pauls (57) ABSTRACT

The present invention relates to a system to control and optimize clinical pathways of a plurality of patients within a medical facility as well as across several medical facilities. The method of controlling and optimizing pathways uses real-time localization devices for patients, resources, such as clinical images and employees of the medical facility (e.g. a service technician, a senior consultant or the like). Based on the local position of patients, staff members and/or resources, the system proposes a medical system that generates clinical pathways for patients, is adapted to change clinical pathways and to provide schedules for patients as well as the use of resources.

The invention provides further means of real-time information of patients about changes in their schedule. The method provided enables a medical facility to streamline their processes and to increase patient throughput.

18 Claims, 2 Drawing Sheets

CONTROLLING AND OPTIMIZING PATIENT PATHWAYS WITHIN AND ACROSS HEALTH CARE FACILITIES

FIELD OF THE INVENTION

The present invention relates to controlling and optimizing patient pathways within and across health care facilities. This is achieved by providing means of localizing a patient or a staff member within a facility or across facilities as well as means of localizing resources such as diagnostic images, medical equipment or diagnostic units across a health care facility, for example a CT scanner (computerized tomography) within the radiology department of a hospital.

BACKGROUND OF THE INVENTION

Over the last decades the number of patients suffering from chronic diseases has dramatically increased, whereas the total expenditures for health care provisions have almost remained constant. This fact has in previous days caused considerable economic pressure on health care providers. To provide an up-to-date service, health care providers or medical facilities need to invest large amounts of money in state-of-the-art modalities, for example magnetic resonance imaging (MRI) scanners or CT-scanners. To make these large investments worthwhile, medical facilities, such as a practice of a family doctor, a radiology department of a hospital, a whole hospital as such or even regional groups of several hospitals and surgeries need to increase their patient throughput in order to amortize their investments.

If, for example, a patient is referred to a radiology department there are several sections you could divide his or her visit into.

In the following parts of the text, for clarity's sake only the male form of a subject is used, without excluding female subjects in the referred context. So the patient may be construed as male or female and vice versa, wherever appropriate.

Sections into which the clinical pathway of the patient could be divided into could be for example: the patient arrives at the radiology department and admits himself to the help desk, the patient waits within the department's waiting area, the patient is about to enter the changing room to get redressed/undressed in order to enter a medical modality, the patient is making his way to the actual modality, such as a CT-scanner, the patient is making his way to the info desk, the patient is returning back to the ward he came from, the patient may be leaving the medical facility, the patient is being examined in another department.

For a medical facility there are in general two different types of patients. Some patients do stay for a certain period of time in one of the wards of the hospital as so called in-patient. There is a second group of patients who deliberately came to the medical facility such as the radiology department for a particular examination or a plurality of specific examinations or a specific treatment. This second group of patients leaves the facility once the particular examination or the specific treatment is finished. This second group of patients is called out-patients. The clinical pathway for in-patients is different from that for out-patients.

Although these are typical clinical pathways a patient has to follow there is just a limited extent to which these clinical pathways can actually be planned and organized. This is simply due to the requirements given within the medical facility, for example a radiology department. Such requirements within the medical facility could be for example: some emergency cases get admitted to the department which need to be treated immediately, some treatments may take longer than expected, one of the resources used such as a scanner may fail due to a hardware break-down.

This may cause several examinations that have been scheduled for a certain time to be rescheduled or moved to a different medical modality, for example instead of an MRI scan one could reroute the patient to a CT scanner in case the MRI scanner dropped out or in response to an urgent emergency scan at the MRI scanner, if planned examination allowed for a CT scan.

Further, it might as well occur that a patient has to travel between different departments of different hospitals because some medical modalities might only be available within a certain department of another hospital. So actually the concept of patient pathways or clinical pathways is not only valid across or within a specialist surgery or a single department of a clinic or several departments within one hospital. The concept of clinical pathways does as well hold for the patient visiting several departments across different hospitals or the patient seeing several specialist consultants.

In order to facilitate the clinical pathways within health care providers, there is a need to control and optimize the clinical pathways within these health care providers. Suppose the MRI scan of a patient Fisher needs to be postponed as there was an emergency case coming in that immediately needs an MRI scan. In order to inform patient Fisher, it is necessary to know whether he is already at the radiology department, making his way to the radiology department, already in the changing room, at the restrooms or just waiting in the waiting area of the radiology department.

Up until now, it is the task of the staff working at the medical facility, for example the radiology department, to actually retrieve the patient and inform him about the change of schedule and the postponed MRI scan.

The patient could either be retrieved via some loudspeaker announcement, by personal follow-up or staff seeking the patient Fisher, probably checking the corridors between the ward the patient came from and the radiology department.

This process is inefficient, time-consuming and binding resources. As a consequence, other tasks with respect to employee, staff or nurse etc. are suspended/delayed.

Thus, exact localization of patients can help to overcome such losses in efficiency and to streamline processes.

It will be appreciated by the person skilled in the art that there is a need to clearly localize the patient at a given time in order to streamline processes or clinical pathways within medical facilities.

Furthermore, also mobile resources, such as medical equipment, clinical images, documents and the like need to be localized.

It might very well happen that some resources, for example a mobile ultrasound unit or just printed clinical images (maybe images from an MRI scan), need to be retrieved before a radiologist could actually stage a cancer or carry out any other diagnostic steps for which these clinical images are crucial to come to a diagnosis.

Although a clinic is supposed to be well-organized, it might easily happen that an image is supposed to be within the radiology department when in fact it is currently making its way to the patient's ward. This may be because the ward has initiated cancer staging for patient Fisher after a senior consultant referred him to the radiology department when visiting the ward. Hence the ward may request the clinical images such that the senior consultant can see them next time he visits the patient at the ward.

So again, finding the resources such as a mobile ultrasound scanner or some clinical images is time-consuming and an inefficient use of time and manpower.

Considering the said, a need for an automated process to support such scenarios is taking shape. Ideally this should be done automatically and without a person necessary to find these resources.

Retrieving patients or resources could as well be done in a semi-automatic way such that the system states that patient Fisher's x-ray images are within the internal ward and not as expected within the radiology department. Once this information is retrieved, in a semi-automatic system an employee of the radiology department could be sent to the internal ward to actually pick up the x-ray images of patient Fisher.

It is not only the resources and patients one would like to know their whereabouts at a given point in time. It is also the clinical pathways that probably need to be changed due to an emergency case as stated above. If this change in pathways is done by a person, it would be a rather time-consuming process as several pathways of a plurality of patients need to be taken into account as well as all available resources, such as MRI or x-ray scanners that are within the medical facility and a plurality of examinations that have been scheduled for a certain point in time.

It will be apparent to a person skilled in the art that this task could be very well solved by an automatic system to rearrange/reschedule and optimize clinical pathways of the patient or a plurality of patients within any medical facility, in case there was an ad-hoc change of schedule due to, for example, an emergency patient.

It is one aspect of the present invention to provide means of localizing either a plurality of patients and/or a plurality of resources.

Within the remainder of this disclosure resources are to be construed as devices or objects needed to carry out a step within a clinical pathway. There are mobile resources such as for example a mobile ultrasound scanner or diagnostic images of a patient. Further within the context of this disclosures individuals working within the medical facility, such as clinicians, employees, nurses and the like shall be referred to as human resources. Some of the resources present within a medical facility do not change their location, such as for example an MRI scanner.

According to another aspect of the invention, means of localization are achieved for example by means of using special cameras within the hospital and/or an RFID chip that is attached to a patient or attached a resource such as a mobile ultrasound unit or clinical images of a patient. RFID is standing short for Radio Frequency Identification.

The present invention allows localizing a patient out of a plurality of patients or a resource out of a plurality of resources. Within a next step of dealing with patient pathways and resources it would be possible to deliberately inform a specific patient that his scheduled examination has been postponed. Alternatively one could inform the patient that his schedule had been rearranged. His blood test was preponed before the MRI scan that initially was scheduled before the urography and having a blood sample taken.

According to a further aspect of the invention, due to the exact localization of the patient, it is possible to inform the patient by some means of graphical display that there was a change of plan and he is now supposed to go the urology department instead of staying within the waiting area of the radiology department.

The provision of information to the patient after a change in the clinical pathway could as well be done as a semi-automatic process, without any limitation.

According to a further aspect of the invention a clinical system would inform the employees of the medical facility, for example the radiology department that patient Fisher is sitting within the waiting area. Then a staff member would actually address him personally and tell him that he has now to go to the urology ward to get an urography done before MRI scanning the kidneys for any deformation that could not be recognized within the x-ray urography.

With the above it has been clearly explained that there is a need within the field of controlling and optimizing clinical pathways of patients within and across health care facilities and a need of precisely localizing the patients or the resources. This means of localizing could be for example done by means of RFID technology, a cellular phone, a camera or any other localization device, preferably a contact-less localization device.

One could also locate a staff member e.g. with a certain clinical and/or language skill required in case of emergency.

SUMMARY OF THE INVENTION

According to an aspect of the invention, there is a method provided to control at least one clinical pathway for a patient in a medical facility comprising the steps of:
Providing at least one clinical pathway with a plurality of necessary process steps out of a plurality of all possible process steps;
Determining resources for carrying out the necessary process steps;
Identifying a local position of the patient;
Identifying local positions of at least one resource being determined;
Controlling a clinical pathway by means of determining a schedule for the necessary process steps, based on the identified local position of the patient and on the identified local positions of the resources.

A medical facility within the context of this disclosure should refer to either a practice of a family doctor or a specialist doctor, a department within a hospital, such as for example a radiology department, a plurality of departments within a hospital, a hospital as a whole comprising several departments, as well as several surgeries, hospital departments and hospitals within a region that are not necessarily at just one place and which might be affiliated to build a super ordinate medical facility.

Process steps are defined as the stages a visit of the patient to the medical facility can be divided into. Such process steps could be for example: entering the department, the patient making himself known to the info desk, the patient waiting in the waiting area, getting undressed within a changing room, waiting for the examination, getting the actual examination, for example a blood sample taken, an x-ray image taken, an MRI scan and the like until the patient leaves the health care provider for either moving to the next health care provider or just to finish the clinical pathway. A clinical pathway might comprise several sub-pathways, each being associated with one hospital visit, a period of being an in-patient for a specific period and so on.

Plurality of items is defined within this disclosure as a group of items that consists of at least one item or more than one item.

A clinical pathway consists of a sequence of process steps. Once a sequence of a plurality of process steps is selected out of all possible process steps within the medical facility, a clinical pathway is formed comprising the selected process steps as necessary process steps to pursue the clinical pathway. If an example within this disclosure mentions a clinical pathway, such as for example in "a clinical pathway is provided by the clinical system", it may refer to one or a plurality of clinical pathways.

A patient, as used throughout this disclosure, refers to a single patient as well as a plurality of patients. In this sense the given examples within this disclosure do not only hold for a single patient but also for a plurality of patients. It is quite obvious for a medical center that there may be more than one single patient.

Resources concurrently refer to human resources or mobile resources. Human resources refer to people participating as service providers within a clinical pathway, such as clinicians, practitioners, nurses, care nurses, drivers for patient transportation, as well as technicians maintaining devices or technical resources.

Mobile resources are movable objects playing a part within a clinical pathway. For example, this could be a clinical image or a mobile ultrasound scanner.

Some resources are normally neither mobile nor human such as an MRI scanner. Resources within this disclosure may refer to more than one resource of the above kinds and/or a single resource.

A local position of a patient is defined as the place at which the patient is located at a given point in time, such as for example: the patient is now sitting in waiting room No. 2 in front of x-ray scanner No. 5.

A local position of a resource is defined accordingly as the place at which the resource is located at a given point in time.

Controlling the clinical pathway can be done by determining a schedule for the necessary process steps based on the identified local position of the patient and on the identified local position of the resources. Furthermore, controlling the clinical pathways might as well mean to reschedule the patient's pathway, once there was an unexpected event that for example caused the patient's MRI scan to be postponed, for example because there was an emergency case.

Further the identified local position for a given patient or the identified local position for a given resource allow to track the whereabouts of the given patient and/or the given resource, respectively. That means one is able to tell where the patient and/or the resource is located currently. More precisely, where and when was the patient and/or the resource located for the last time. This will be explained in more detail within the detailed description of the invention.

The provision of the clinical pathway according to a further aspect of the invention may mean to generate at least one new clinical pathway for the patient or to modify a plurality of existing clinical pathways.

Supposed there is a patient Fisher who was referred to the medical facility for getting some blood tests together with an x-ray urography and an MRI scan of the prostate. If now unexpectedly an MRI scan of an emergency patient was necessary this would mean the MRI scanner would not be available for the prostate scan of the patient Fisher. If now within the provided clinical pathway of the patient Fisher the first step would have been the MRI scan, followed by the urography within the x-ray department and then some blood sample to be taken within the inner ward. After the emergency within the MRI department occurred, it might be more efficient to first send the patient Fisher to give the blood sample within the inner wards then move to the x-ray urography examination and just thereafter enter the MRI department again. This rearrangement of appointments, i.e. the clinical pathway saves the patient Fisher from waiting within the MRI department for quite a long time and actually makes efficient use of time if, for example, there was some free capacity within the x-ray department or the inner department for taking blood samples.

The method, according to the present invention, wherein the provision of a clinical pathway comprises the following steps:

Receiving relevant parameters,
Determining necessary process steps for the clinical pathway, comprising determining at least one medical modality;
Considering relevant parameters, time-related parameters, position-related parameters and the necessary process steps for the clinical pathway.

Relevant parameters are defined within this disclosure as a plurality of parameters that are in any respect relevant to the patient traveling along the clinical pathway, for example the patient being a diabetic, the head and neck scan taking 20 minutes, a contrast agent needed for a MRI angiography, an incompatibility of the contrast agent with other contrast agents or medications. Again, relevant parameters refer to a plurality of parameters such that there may be only a single relevant parameter and/or more than one parameter that is relevant.

Medical modality refers to a modality that is linked to a process step or a necessary process step as part of a clinical pathway. So for example the medical modality of an MRI head and neck scan for the patient is MRI. There may be process steps which are related to more than one single medical modality.

According to a further aspect of the invention, the method of providing the clinical pathway for a given patient has to take into account all the necessary process steps that have been scheduled for the patient, such as admitting him to the radiology department, getting an MRI scan in the radiology department, transferring him to the urology department, getting the urography done and returning the patient to the ward he is staying at, in case he is an in-patient or providing means of patient transportation so that he actually gets home to his house or a nursing home in case the patient is not mobile enough to go there by himself.

The identification of the local position of a patient or a resource can be based on a real time localization system. A Real Time Localization System could for example be implemented by using RFID technology (short for Radio Frequency Identification).

Without any limitation of the invention any other technology could be used to implement a real time localization system.

According to one aspect of the present invention, at least one patient and/or at least one resource being determined are equipped with an RFID transponder or an RFID tag and the medical facility is equipped with at least one RFID reader. So the RFID reader would read the RFID tags that are within the reach of a given RFID reader, such that the patient or the resource can be localized as soon as they appear within the scope of a given RFID reader.

Alternatively, according to a further aspect of the present invention, the identification of the local positions can be based on WLAN (Wireless LAN).

Further, the identification of the local positions, according to the present invention, can be based on optical determination by means of a camera. Such a camera could be for example and without limitation a 3D camera.

The controlling of clinical pathways, according to the present invention, can be done in real time.

According to a further aspect of the present invention, it is possible that all necessary process steps or only a selection out of the process steps are carried out automatically.

So it may very well be, according to a further aspect of the invention, that the information of the patient regarding the change in schedule and/or clinical pathway is being delivered by an employee or alternatively just by a graphical display.

According to another aspect of the invention, a result of the controlling comprises:

Determining alternative process steps,

Generating a forecast for the clinical pathway or for separate necessary process steps, comprising notifying about possible delays.

It will be appreciated by a person sufficiently skilled in the art that the step of determining alternative process steps would allow the medical facility to flexibly respond to circumstances under which one or more of the resources, such as an MRI scanner, are down due to maintenance being carried out. In such a situation an x-ray scan may be in some cases an appropriate alternative process step that could replace the original necessary process step of the respective MRI scan the patient was scheduled for.

The capability of the present invention to generate a forecast will surely be appreciated by a person skilled in the art. The forecast would help the patient to decide whether it is worthwhile to do some other activities before he is due for the rescheduled process step such as the head and neck MRI scan. Alternatively, the ward the patient is staying at would send the patient at a later point in time to the radiology department if they were informed that the scan was delayed.

Notifying the patient about possible delays may be achieved for example by graphical means or loud speaker announcements, as explained above.

Result of the controlling may affect a plurality of clinical pathways.

Method of controlling and optimizing clinical pathways, according to a further aspect of the present invention, wherein a result of the control of the clinical pathway or a plurality of clinical pathways is displayed graphically, and may comprise a time schedule for each of the necessary process steps and/or the clinical pathway as a whole.

It is this schedule that actually guides the patient through the health care facility. Means of graphically displaying this schedule actually helps to inform the patient of any possible changes of his scheduled examinations or the like. It will be appreciated by a person skilled in the art that changes in the clinical pathway of the patient may be graphically displayed on the walls or on the floor of a room the patient is located in. Obviously these means of graphical display may be static or changing in time. Such means for graphical display are well known, for example display monitors, projecting devices, laser systems and the like.

Under the same circumstances it may sometimes be convenient to inform the patient about changes in schedule via his cellular phone, pager or another mobile electronic device e.g. in case the patient is still on his way to the medical facility.

If the present invention, according to a further aspect, would take care of informing patients or other medical facilities about delays for the patient traveling along his clinical pathway, the workload for the staff would be remarkably reduced. The staff would be enabled to focus on core tasks again.

According to an aspect of the present invention, the method of controlling and optimizing clinical pathways comprises:

assigning a unique electronic patient identification to at least one of the patients and/or assigning a unique electronic resource identification to at least one of the resources;

assigning a time stamp to each one of the local positions being identified.

The use of a real time localization technology, such as RFID, for the localization of the patients and the resources does conveniently provide means of the assignment of a unique electronic patient identification to at least one of the patients and/or a unique electronic resource identification to at least one of the resources. This would further allow identifying patients and/or resources whenever one of them passes a given RFID reader.

The assignment of a time stamp to each of the local positions being identified for a given patient or a resource would allow tracking the whereabouts of a patient or a given resource.

So for example one could know that at 2:00 pm the mobile ultrasound unit passed an RFID reader at the maternity ward for the last time. Therefore it is quite likely for the mobile ultrasound unit to still be at the maternity ward at a location where it cannot be read by an RFID reader. Alternatively, if the patient passed the RFID reader 20 minutes ago at the rest rooms and there was no further contact with an RFID reader since then, it is quite likely for the patient that there was an accident, e.g. a diabetic patient just fainting when being at the rest rooms.

The method of controlling and optimizing clinical pathways within and across medical facilities, whereby the method and in particular the steps of identifying and controlling are carried out for a given point in time.

The method could for example be used to check whether there are any x-ray examinations scheduled for the radiology department for a given time. Suppose the MRI scanner broke down for 1 hour at 3:00 pm due to some hardware being exchanged, such as a gradient unit at 2:45 pm. The patient Fisher was originally due for an MRI scan at 3:00 pm. In case the patient Fisher was scheduled for an MRI scan and an x-ray examination, the x-ray examination could be carried out before the MRI scan. If he was due for an MRI scan only, the x-ray examination may be a replacement of the MRI scan, if that was appropriate for the examination of patient Fisher.

Hence, according to a further aspect of the invention, it is possible to find out how much resources are being used just now and/or if there are any free capacities that could be used alternatively.

A clinical system for a medical facility comprises:

a controller for controlling a plurality of clinical pathways for at least one patient within the medical facility;

a clinical pathway generation module for providing a plurality of clinical pathways with a plurality of necessary process steps out of all possible process steps;

a resource determination module for determining resources for carrying out the necessary process steps;

a plurality of local position identifiers for identifying a local position of at least one patient and/or of the plurality of resources being determined, wherein the controller is adapted for controlling the clinical pathway for at least one patient by means of determination of a schedule for the plurality of necessary process steps based on the identified local position of at least one patient and/or on the identified local position of the plurality of resources being determined.

The controller can be a hardware module and/or a software module that provides means of controlling a plurality of clinical pathways of the patients within the medical facility.

Although the disclosure does speak of one controller only, there may be without any limitation more than one controller within the clinical system, for example, if the clinical system is distributed over several hospitals.

The clinical pathway generation module is defined as a software and/or hardware module that is capable of generating clinical pathways for a plurality of patients. Although the disclosure does only speak of one clinical pathway generation module, there may be without any limitation more than one clinical pathway generation module within the clinical system, for example, if the clinical system is distributed over several hospitals.

The resource determination module is defined as a hardware and/or software module to determine the resources needed to carry out necessary process steps within the clinical pathway. Although the disclosure does only speak of one resource determination module, there may be without any limitation more than one resource determination module within the clinical system, for example, if the clinical system is distributed over several hospitals.

The local position identifiers can conveniently be implemented as RFID tags or RFID transponder and the system further comprising at least one RFID reader for reading and/or processing local position information, provided by the RFID transponders that are connected to either the resources or the patients.

The system for optimizing and controlling patient pathways within and across health care facilities can be arranged as a computer program product such that it can be executed on a computer or a computer system.

It should be noted that the computer program product may very well be executed on different computers that are remote to each other.

DETAILED DESCRIPTION OF THE INVENTION

Figure 1A:
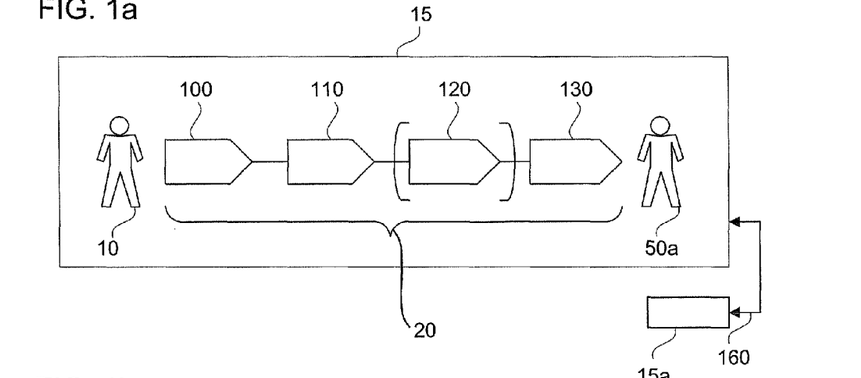
FIG. 1a shows an archetypical clinical pathway.

FIG. 1a shows an archetypical clinical pathway 20 of a patient 10 within a single medical facility 15 comprising a step of admission 100, examination 110, and optional treatment 120, followed by a discharge 130 of the patient 10. The clinical pathway 20 at just a single medical facility 15 could for example be the patient 10 visiting his family doctor. Supposed the patient 10 visits his family doctor, so he gets admitted/admits himself to the doctor, he gets examined by his family doctor, who can be considered within this disclosure as a human resource 50a.

The family doctor may find out that the patient's 10 body temperature is elevated, that the patient 10 is coughing, feels tired, dizzy and complains about body aching. Hence, the family doctor may conclude that the patient 10 is having a cold. The family doctor may write a prescription 160 for the patient 10 which the patient 10 may get from a pharmacy, the pharmacy being a second medical facility 15a in the framework of this disclosure.

After the prescription 160 has been written, the patient 10 gets discharged 130 and leaves the practice of the family doctor or in a more general context leaves the medical facility 15.

Obviously, the clinical pathways 20 as depicted in FIG. 1a highly depend on the condition of the patient 10. There might be clinical pathways 20 that hardly ever change, like in cases of renal dialysis. The patient 10 in such a case for example, would be weekly admitted to an appropriate medical facility 15, where he receives renal dialysis as treatment 120, and gets discharged 130.

In FIG. 1a the clinical pathway 20 was depicted for the patient 10 visiting only one single medical facility 15. It happens quite often that the patient 10 has a clinical pathway 20 that is characterized by visiting more than one medical facility 15, for example a radiology department or an internal ward or the hospital itself.

Figure 1B:
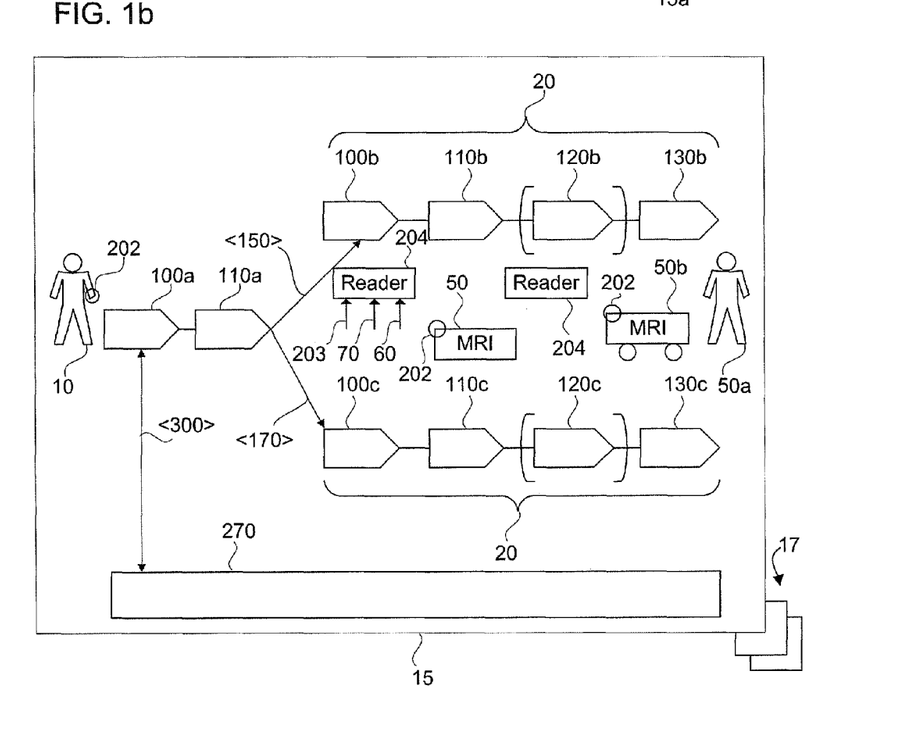
FIG. 1b shows a clinical pathway for a patient comprising more than one medical facility.

FIG. 1b shows the clinical pathway for the patient 10 who is showing specific symptoms and admits himself to hospital. He is for example complaining about severe abdominal pain that hardly permits him standing straight and tells the personnel that he had a history of kidney stones. Hence he might be referred as an emergency 170 to the urology in-patient clinic, where a urography is carried out.

During the same visit the medical facility 15 may refer the patient 10 to an internal ward to get a blood screening done to find out if any blood values are indicative towards the reason of the patient's symptoms.

According to another aspect of the present invention, the invention is capable to optimize and control the clinical pathways 20 of the patients 10 within the medical facility 15 and across medical facilities 15. According to one aspect of the present invention, it helps to streamline the clinical pathways, processes, protocols and workflows.

According to a further aspect of the present invention, it helps to increase patient throughput a medical facility 15 achieves which helps optimizing economic costing.

It is a further aim of the present invention to improve patient throughput for the medical facility 15, as well as reducing waiting times for the patients 10.

The present invention is not only capable of streamlining, i.e. optimizing and controlling clinical pathways 20 within a single medical facility 15, but also across different medical facilities. It might be that a family doctor refers the patient 10 to a urology ward to check if the patient 10 has kidney stones or not, as well as the family doctor may further refer the patient 10 to a radiology department to check whether there might be another reason for the abdominal pains the patient 10 is complaining about.

Such a referral 150 may happen as an emergency referral or just as a normal referral. The referral 150 may further happen across different hospitals, clinics, surgeries of clinicians or specialists.

To optimize the clinical pathways within the medical facility the present invention relies on localization devices. More precisely it does actually provide a real time localization system.

The localization devices used within the present invention could for example be implemented by means of RFID devices. RFID is standing short for Radio-Frequency-Identification. RFID technology allows attaching a Radio-Frequency circuit, an RFID tag 202 to an object or a person. When passing an RFID reader 204, the RFID tag 202 attached to the person or the object will respond to the RFID reader 204 by providing a unique identification number, i.e. an ID 203 that can be used to identify the person or the object that is attached to the RFID tag 202.

RFID technology actually allows quite convenient means of identifying objects. RFID is a contact-less method of identifying objects and persons. There are different types of RFID devices, they could either be passive, which means that the RFID-tag 202 does not have its own power supply but reflects or backscatters the RF power transmitted by the RF reader 204 which allows to identify the RFID tag 202 via the ID 203 being received by the RFID reader 204.

The RFID tag 202 could be an active 202 or a semi-active RFID tag, which means the RFID tag 202 actually comes with its own power supply. Normally RFID tags 202 can be read by RFID readers 204 over distances ranging from about 10 centimeters up to a few meters. If actually active RFID tags were to be used, they would be able to communicate their ID 203 to the RFID reader 204 in surroundings that are more challenging in terms of RF conductivity. A situation being challenging in terms of RF conductivity particularly holds for situations where an RF load, most commonly water, is in close vicinity of the RFID tag 202 or the RFID reader 204. For example, a person or an animal would actually be a rather RF challenging surrounding for an RFID tag 202 as well as for the RFID reader, as the body water content would make the backscattering of the RF power transmitted by the RFID reader 204 more difficult. In such a case of challenging RF surroundings the use of an active RFID tag 202 would make the transmission of the ID 203 to the RFID reader 204 more reliable.

The ID 203 of the RFID tag 202 transmitted back to the RFID reader 204 would identify the local position 70, 60 of the RFID tag 202 as being in close vicinity of the RFID reader 204.

So to provide means of identifying the local positions 70, 60 of resources 50 or patients 10 it is necessary to provide a sufficient number of RFID readers 204 throughout the medical facility 15. Typically there would be a plurality of RFID readers 204 distributed across the medical facility 15 to ensure that the whole area of the medical facility 15 is covered by a plurality of RFID readers 204.

Conveniently the respective area of reception for adjacent RFID readers 204 does not intersect too much, such that there is a unique RFID reader 204 that receives the ID 203 from the RFID tag 202.

According to a further aspect of the invention, the plurality of all RFID readers 204 present within the medical facility 15 would be connected to a medical system 220 that receives the response from RFID tags 202 that have been within the range of the plurality of RFID readers 204. Conveniently this can be done by means of a real-time localization database 240 wherein for a given RFID tag 202 the position of the RFID reader 204 that receives the ID 203 from the RFID tag 202 is stored together with a time stamp. The plurality of RFID readers 204 would be connected via an appropriate network, such as for example a TCIP network or an appropriate bus system, with the medical system 220. Hence all the IDs 203 from RFID tags 202 that were received by RFID readers 204 are communicated to the medical system 220.

Further to identifying the whereabouts of the patient 10, the present invention is also capable of finding a local position 70 of resources 50. Such resources 50 could be a clinical image as a mobile resource 50b. An employee of the medical facility 15, would comprise a human resource 50a. A general resource 50 would be a device, for example an MRI scanner that normally does not change its location.

The medical system 220, according to the present invention, provides means of optimizing and controlling clinical pathways 20 even across several medical facilities such as in hospitals and surgeries within a geographical area as explained above.

Figure 2:
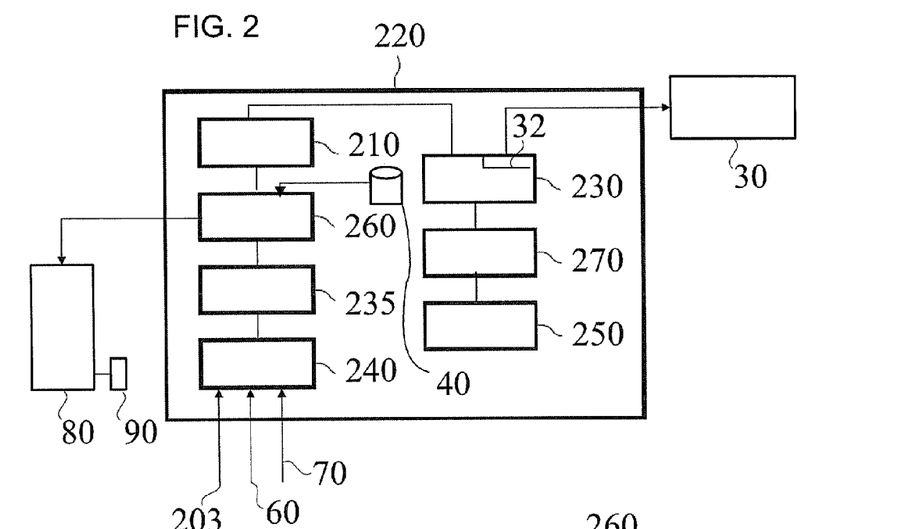
FIG. 2 shows a diagram of modules comprising a clinical system for controlling and optimizing clinical pathways.

FIG. 2 shows a block diagram indicating the medical system 220 comprising several components. These components are a controller 210, a clinical pathway generation module 260, a database 235 with asset information, a real time localization database 240, a central scheduling server 230, a financial logic module 270 and a medical rule engine 250. The medical system 220 and/or individual components thereof may use for example logic, probabilistic approaches or fuzzy logic to control and optimize clinical pathways 20.

The present invention makes use of clinical pathways 20 and localization devices such as RFID tags 202, RFID readers 204, PDAs, video cameras, cellular phones and the like, for optimizing the clinical pathways 20 across a single healthcare facility 15 or even across a plurality of healthcare facilities 15.

The medical system 220 performs healthcare resource 50 scheduling based on
- symptoms of the patient 10,
- clinical guidelines,
- diagnostic questions from the physician,
- search key words, i.e. the search for a medical expert within a certain geographic region, for example a cardiovascular expert in the region of Austin, Tex.;
- availability of the resources 50,
- a business logic 300 of medical facilities 15, taking part in a network of medical facilities 17,
- the localization devices, (for example RFID devices) to guide patients 15 and staff members, i.e. human resources 50a within the medical facility 15
- identification of necessary process steps 80 within a care plan and the like.

The pathway generation module 260 is capable of generating the clinical pathway 20 for a given patient 10, for example patient Fisher.

The controller 210 is in charge of coordinating the interaction of all modules within the medical system 220 for the control and optimization of clinical pathways 20. The controller 210 may be implemented as hardware and/or software.

The database with asset information 235, according to the present invention, stores all resources 50 available within the medical facility 15 as well as the necessary process steps 80 that have already been allocated for a plurality of patients for the resources 50. For example, it would store all MRI examinations scheduled for today.

According to another aspect of the present invention, a schedule 30 could alternatively be generated by a schedule generation module 32 deducing schedules 30 for given patients 10 or given resources 50 out of the pathway generation module 260.

The real time localization database 240 is adapted to store information about the local positions 70, 60 of all resources 50, 50a, 50b and all patients 10 within the medical facility 15. The real time localization database 240 can provide the medical system 220 with the whereabouts of all patients 10 and resources 50, 50a, 50b at a given point in time.

The content of the real time localization database 240 may, according to another aspect of the invention, be used to track clinical pathways of patients 10 showing a specific condition in retrospect. This solid data material provided by the medical system 220 is well adapted to study clinical pathways 20 in retrospect.

It will clearly be appreciated by a person sufficiently skilled in the art that the information stored within the localization database 240 may be used to re-evaluate clinical protocols for a given condition. This may, for example, lead to a new protocol for emergency cases with kidney stones. With the clinical pathway 20 provided by the pathway generation module 260 an appointment at the MRI department for a soft tissue scan will be allocated as well as an appointment within the urology department to carry out a urography of the patient to see immediately if the patient's 10 ureter is blocked by fat deposits.

Alternatively, it may turn out useful to start the examination of the patient with kidney stones with a ultrasonic scan to find out straight away whether or not the kidneys are blocked and the patient 10 is hence prone to a renal colic, needing a stent to be applied within the ureter as soon as possible to save him from severe pain and acute renal failure.

According to a further aspect of the present invention, the real time localization database 240 will conveniently be updated after a given time interval. It may be convenient for the RFID readers 204 to transmit the received IDs 203 for example every five minutes. For high traffic areas shorter update intervals may be appropriate, as well as longer update periods for rather silent areas, such as an archive room for MRI images.

According to another aspect of the invention, the RFID readers 204 may be provided with a memory sufficiently large to store a reasonable number of IDs 203 within the reach of the RFID reader. This would help to organize the traffic of information to the medical system 220 across the network more efficiently.

According to an alternative aspect of the present invention, it is as well possible to define a very short update period for critical patients (e.g. diabetics). The controller 210 of the medical system 220 could check the last local position 70 of all critical patients and cause those RFID readers in adjacent regions to the critical patients to send updates of the IDs 302 within their reach for example every 30 seconds. This would allow for a very fine spacing of points in time for which the local position 70 of the critical patients is known.

According to a further aspect of the invention, the real time localization database 240 can be used to assess patient compliance. The system provided would allow checking whether the patient gets a prescription from the pharmacy as ordered by the consultant. Alternatively, one could check whether or not the patient attends the physiotherapy appointments he was prescribed in order to help him with back pain.

According to another aspect of the invention, it would be possible for the medical system 220 to set an alarm if the patient stayed for more than X minutes within the rest rooms. A person skilled in the art will appreciate that such an alert would be helpful when dealing with diabetic patients, for example.

Fainting is not improbable for diabetic patients, in case their blood sugar levels are too low. The alert would help the medical facility 15 to get informed about a possible breakdown of the patient when he is out of sight, as for example when being at the rest rooms.

It is possible to track down the whereabouts of a staff member, should he be needed due to an emergency by means of the medical system 220 and in particular the real time localization database 240. The real time localization database 240 would be able to tell where and when the staff member recently passed a given localization device (e.g., a given RFID reader) for the last time.

Up to now this tracking of staff members was done by people who did not necessarily know where the staff member went to.

The medical rule engine 250 is used to consider the clinical condition of the patient 10, his history, medical guidelines, expert knowledge and the like. The medical rule engine 250 may be implemented as hardware and/or software.

So if the pathway generation module 260 was to generate or amend the clinical pathway 20 for a given patient 10, the pathway generation module 260 may interact with the medical rule engine 250 to check the correctness of clinical pathways 20 generated by the pathway generation module 260.

The financial logic module 270 is adapted to evaluate all clinical pathways 20 as indicated by a business logic module 300 within FIG. 1b. The financial logic module 270 may be implemented as a hardware and/or software module. The business logic module 300 may as well be implemented as a hardware and/or software module.

According to one aspect of the invention, the medical facility 15 is capable of doing the billing and book keeping in an automated or semi-automated way. The business logic module 300 would be able to assess all steps a patient 10 had traveled within a given clinical pathway 20. In a next step, the business logic module 300 would forward all services delivered to the patient 10 to the financial logic module 270. From the plurality of services rendered, the financial logic module 270 could draft a bill and/or directly set up a contact to the patient's health insurance company.

The central scheduling server 230 is capable of assigning time values to necessary process steps 80 comprised within the clinical pathway 20 of the patient 10. This gives a timely order to necessary process steps 80 being part of the clinical pathway 20 of the patient 10. For this purpose the central scheduling server 230 is adapted to interact with the pathway generation module 260, the database with asset information 235, the real time localization database 240 and/or the medical rule engine 250.

When the patient 10 travels along a clinical pathway 20 as depicted in FIG. 1a or FIG. 1b, it is crucial to know the location of resources 50 that are needed to carry out necessary process steps 80 of a clinical pathway 20, as well as to schedule the use of these resources 50.

Now the patient 10 is to follow the clinical pathway 20 that has been outlined for the patient 10 due to his condition or the needed examination 110. The clinical pathway 20 comprises several necessary process steps 80, out of a plurality of possible process steps 40. The process steps 40 can be an admission 100 of the patient 10, an examination 110 of the patient 10, a treatment 120 of the patient 10, a referral 150, an emergency referral 170 and the like.

The necessary process steps 80 are selected out of the plurality of all possible process steps 40 within the medical facility 15. Single process steps out of the plurality of all possible process steps 40 are concatenated to form a sequence of process steps forming the clinical pathway 20 of the patient 10. The process steps which are part of the clinical pathway 20 become necessary process steps 80.

Once the necessary process steps 80 for the clinical pathway 20 are determined, a medical modality 90, connected with the necessary process steps 80 has been determined. For example, if the necessary process step 80 is to perform a head and neck MRI scan on the patient 10, the medical modality 90 would be an appropriate MRI scan making use of a specific MRI scanner together with a time-slot needed to carry out the MRI scan.

For controlling the clinical pathway 20 and for determining a schedule 30 for the necessary process steps 80 based on the local position 60 of the patient 10 and on the identified local position 70 of the resources 50, the medical system 220 defines the schedule 30. The schedule 30 comprises local and time information on when a given patient 10 is supposed to have e.g. an MRI scan within the radiology department.

Often a change in the schedule 30 for the patient is necessary as emergencies might occur.

Figure 3:
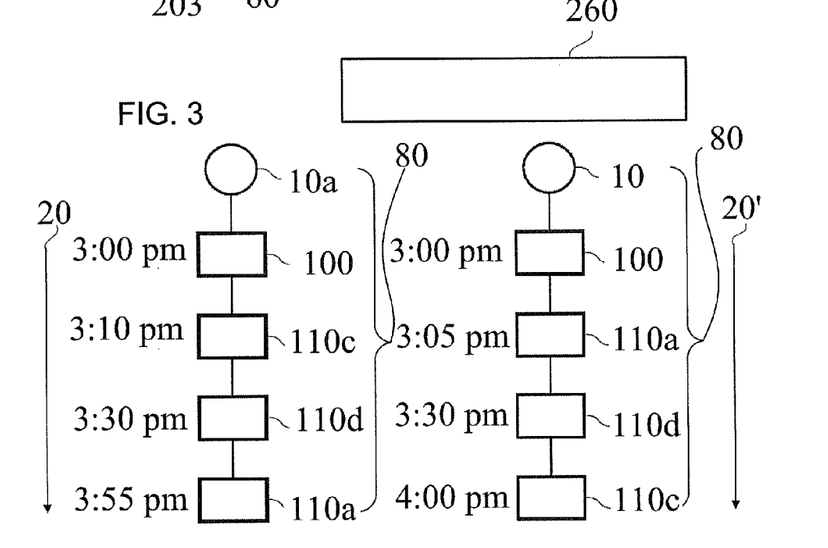
FIG. 3 shows a clinical pathway for a patient that has been rescheduled for the patient.

FIG. 3 shows the original clinical pathway 20 for the patient Fisher 10a together with a scheduled time for each of the necessary process steps 80. So at 3:00 pm, patient Fisher 10a is supposed to admit 100 himself to the info desk. At 3:10 pm a time slot is allocated for the MRI scan of the prostate 110c, at 3:30 pm the patient Fisher is scheduled for an x-ray urography at the x-ray department and at 3:55 pm the patient Fisher 10a is supposed to give blood samples for some blood tests 110a at the hospital lab.

If now, unexpectedly, an MRI scan of an emergency patient 44 was necessary at 3:03 pm, this would mean the MRI scanner would not be available for the prostate scan 110c of the patient Fisher 10a.

After the emergency within the MRI department occurred, it might be more efficient to first send the patient Fisher 10a to give the blood samples at the hospital lab, then move to the x-ray urography examination and just thereafter enter the MRI department again. This rearrangement of appointments, i.e. the clinical pathway 20 saves the patient Fisher 10a from waiting within the MRI department for quite a long time and actually makes efficient use of the time if, for example, there was some free capacity within the x-ray department or the hospital lab for taking blood samples.

If the medical system 220 receives a message about the emergency patient 11 at the MRI scanner, it would reorganize the clinical pathways 20 for a plurality of patients that were originally scheduled for an MRI scan for today later than 3:03 pm when the emergency patient 11 arrived. The patient Fisher 10a will be within this group of patients 10.

The medical system will in a first step identify all patients 10 that were scheduled for an MRI scan at a time later or equal 3:03 pm today. The pathway generation module 260 will then try to re-organize or re-shuffle the plurality of necessary process steps 80 wherever this is possible. To check whether re-arrangements in clinical pathways 20 are possible, the central scheduling server 230 is used to prevent double bookings of the resources 50 or the patients 10 at a given point in time. The central scheduling server 230 is further informed about amended or new clinical pathways 20, implying amended or new schedules 30 for patients 10 or resources 50, 50a, 50b.

FIG. 3 shows on the right hand side an example of a rearranged clinical pathway 20' for the patient Fisher 10a. The patient Fisher 10a is still supposed to admit himself to the info desk at 3:00 pm. The time-order of the following necessary process steps 80 for the patient Fisher 10a has been changed as well as the sequence of necessary process steps 80 by the pathway generation module 260 and/or the central scheduling server 230 as follows.

At 3:05 pm the patient Fisher 10a is expected at the hospital lab to give blood samples for the blood tests 110a. After this event, the x-ray urography 110d is scheduled for 3:30 pm, followed by the MRI scan of the prostate 110c. Thereafter the patient Fisher is discharged from the medical facility 15.

The central scheduling server 230 is not only capable of re-arranging a schedule 30 for a patient 10 as in the above example but as well to give a schedule for the order in time at which for example patients 10 are booked for an MRI scan today.

Clinical pathways 20 are linked to the condition of the patient 10 based on best clinical practice. So in the process of the generation of pathways 20 by the pathway generation module 260, the pathway generation module 260 may rely as well on medical rules stored within the medical rule engine 250.

According to the state of the art, control and optimization of the clinical pathway 20 of the patient 10 would have been done by employees of medical facility 15 such as a nurse, an assistant nurse or even a clinician within a medical facility 15.

According to one aspect of the present invention, the process of determining the schedule 30 for a plurality of patients 10 within the medical facility 15 would be streamlined if the optimization of the plurality of clinical pathway 20 were carried out fully automatic or in a semi-automatic way.

An advantage of having an automatic or a semi-automatic method for designing schedules 30 for a plurality of clinical pathways 20 will help to increase the patient throughput and enhance efficiency of the employees working within the medical facility 15.

The step of informing the patient 10 may, according to one aspect of the invention, be achieved by optical means that are displayed on walls of rooms the patient 10 is located in. These graphical means may be static or changing in time. Alternatively one could contemplate the displaying of messages to the patient 10 on the floor he is standing and/or staying at, such as "Mr. Fisher please see the information desk, there was a change in your schedule 30 of examinations today".

The information of the patient 10 may alternatively be achieved in an acoustical way by means of a loudspeaker announcement in the room the patient is located in.

In a semi-automatic method a staff member could inform the patient 10 of the change.

Optionally it would be possible to inform the patient 10 about a change in schedule 30 using his cellular phone, pager or another mobile electronic device, in case the patient is still on his way to the medical facility 15.

Likewise, the information of staff members about a change in schedule 30 is achieved by graphical means. For example, the new list of MRI scans scheduled for today could be displayed on a screen.

What is claimed is:

1. Computerized method for controlling a clinical pathway for a patient in a medical facility, comprising the steps of:

Defining at least one clinical pathway with a pathway generation module, the pathway generation module defining for at least one patient a plurality of necessary process steps out of a plurality of all possible process steps;

Determining resources for carrying out the necessary process steps including at least one human medical resource and/or at least one equipment resource for carrying out the necessary process steps;

Tracking in real time with a plurality of localization devices a position of said at least one patient as the patient advances along said at least one clinical pathway;

Tracking in real time with the plurality of localization devices a position of said at least one human medical resource and/or equipment resource for carrying out the necessary process steps;

Identifying a respective real time local position of the patient and said at least one human medical resource, wherein the identifying of the respective real time local position of said at least one patient and said at least one human medical resource is each performed at a selectable rate;

relating an expected level of traffic in said at least one clinical pathway to a respective present local position of the patient and a respective present local position of said at least one human medical resource;

Selecting the respective rate for the identifying of the respective real time local position of said at least one patient and for the identifying of the respective real time local position of said at least one human medical resource based on the expected level of traffic related to the respective present local position of the patient and the respective present local position of said at least one human medical resource;

Identifying a respective real time local position of said at least one equipment resource;

Controlling the clinical pathway by way of a controller configured to determine a schedule for the necessary process steps, the controlling based on the respective identified local position of the patient, the respective identified local position of said at least one human medical resource, and/or the respective identified local position of said at least one equipment resource.

2. Method according to claim 1, wherein providing a clinical pathway comprises generating at least one new clinical pathway and/or modifying a plurality of existing clinical pathways.

3. Method according to claim 1, wherein the method comprises:
Receiving relevant parameters;
Determining necessary process steps for the clinical pathway, comprising determining at least one medical modality;
Considering relevant parameters, time-related parameters, position-related parameters and the necessary process steps for the clinical pathway.

4. Method according to claim 1, wherein equipment resources may comprise mobile resources and/or resources that normally do not change their location.

5. Method according to claim 1, wherein identifying the local position is based on RFID technology, wherein at least one patient and/or at least one resource being determined are equipped with an RFID transponder and the medical facility is equipped with at least one RFID reader.

6. Method according to claim 1, wherein the identification of the local position is based on WLAN.

7. Method according to claim 1, wherein the identification of the local position is based on optical determination by means of a camera.

8. Method according to claim 1, wherein the controlling is done in real time.

9. Method according to claim 1, wherein all of the necessary process steps or a selection of the necessary process steps are carried out automatically.

10. Method according to claim 1, wherein a result of the controlling comprises:
Determining alternative process steps;
Generating a forecast for the clinical pathway or for separate necessary process steps, comprising notifying about possible delays.

11. Method according to claim 10, wherein the result of the controlling is displayed graphically, comprising a time schedule of each of the necessary process steps and/or the clinical pathway as a whole.

12. Method according to claim 1, wherein personalized information comprising schedule information related to a clinical pathway for at least one patient or at least one staff member is automatically communicated only to the person's location by a telecommunicative device comprising at least one of a loudspeaker and a graphical display.

13. Method according to claim 1, wherein the method comprises:
assigning a unique electronic patient identification to at least one of the patients and/or assigning a unique electronic resource identification to at least one of the resources;
assigning a time stamp to each of the identified local positions.

14. Method according to claim 1, wherein the method and particularly the steps of identifying and/or controlling are carried out for a given point in time.

15. Method according to claim 1, further comprising tracking data indicative of clinical pathways of patients and associating said clinical pathways to respective medical conditions of the patients, and processing said data indicative of clinical pathways of patients to evaluate a respective clinical protocol for treating a respective medical condition.

16. Clinical system for a medical facility, comprising:
a controller configured to control a plurality of clinical pathways for at least one patient in the medical facility;
a clinical pathway generation module configured to provide a plurality of clinical pathways with a plurality of necessary process steps out of all possible process steps;
a resource determination module configured to determine resources for carrying out the necessary process steps including at least one human medical resource and/or at least one equipment resource for carrying out the necessary process steps;
a plurality of localization devices arranged to track a real time position of said at least one patient as the patient advances along one of the plurality of clinical pathways, the plurality of localization devices further arranged to track a real time position of said at least one human medical resource, wherein the plurality of localization devices is configured to identify a respective local position of said at least one patient and to identify a respective local position of said at least one human medical resource, wherein the controller relates an expected level of traffic in said at least one clinical pathway to a respective present local position of the patient and a respective present local position of said at least one human medical resource, wherein the identification of the respective real time local position of said at least one patient and said at least one human medical resource is each performed at a selectable rate based on the expected level of traffic related to the respective present local position of the patient and the respective present local position of said at least one human medical resource, wherein the plurality of localization devices is further configured to identify a respective local position of said least one equipment resource;
wherein the controller is adapted to control the clinical pathway for said at least one patient by way of a determination of a schedule for the plurality of necessary process steps, based on the respective identified local position of said at least one patient, the respective identified local position of said at least one human medical resource and/or on the respective identified local position of said least one equipment resource.

17. Clinical system according to claim 16, wherein the local position identifier is an RFID transponder and wherein the system further comprises at least one RFID reader for reading and/or processing local position information, provided by the RFID transponders.

18. Clinical system for a medical facility, comprising:
a controller configured to control a plurality of clinical pathways for at least one patient in the medical facility;
a clinical pathway generation module configured to provide a plurality of clinical pathways with a plurality of necessary process steps out of all possible process steps;
a resource determination module configured to determine resources for carrying out the necessary process steps including at least one human medical resource and/or at least one equipment resource for carrying out the necessary process steps;
a plurality of localization devices arranged to track a real time position of said at least one patient as the patient advances along one of the plurality of clinical pathways, the plurality of localization devices further arranged to track a real time position of said at least one human medical resource, wherein the plurality of localization devices is configured to identify a respective local position of said at least one patient and to identify a respective local position of said at least one human medical resource, wherein the controller relates an expected level of traffic in said at least one clinical pathway to a respective present local position of the patient and a respective present local position of said at least one human medical resource, wherein the plurality of localization devices is further configured to identify a respective local position of said least one equipment resource;

wherein the controller is adapted to control the clinical pathway for said at least one patient by way of a determination of a schedule for the plurality of necessary process steps, based on the respective identified local position of said at least one patient, the respective identified local position of said at least one human medical resource and/or on the respective identified local position of said least one equipment resource; and a database configured to track data indicative of clinical pathways of patients and to associate said clinical pathways to respective medical conditions of the patients, wherein said data indicative of clinical pathways of patients are processed to evaluate a respective clinical protocol for treating a respective medical condition.

* * * * *